United States Patent [19]

Baker et al.

[11] Patent Number: 5,391,579
[45] Date of Patent: Feb. 21, 1995

[54] DEUTERATED SEVOFLURANE AS AN INHALATIONAL ANESTHETIC

[75] Inventors: Max T. Baker; John H. Tinker, both of Iowa City, Iowa

[73] Assignee: University of Iowa Research Foundation, Iowa City, Iowa

[21] Appl. No.: 76,582

[22] Filed: Jun. 14, 1993

Related U.S. Application Data

[62] Division of Ser. No. 10,264, Jan. 28, 1993, abandoned.

[51] Int. Cl.$^6$ ............................................. A61K 31/08
[52] U.S. Cl. .................................................. 514/722
[58] Field of Search ......................................... 514/722

[56] References Cited

U.S. PATENT DOCUMENTS

| | | | |
|---|---|---|---|
| 3,346,448 | 10/1967 | Gilbert | 514/722 |
| 3,476,860 | 11/1969 | Croix | 514/722 |
| 3,683,092 | 8/1972 | Regen | 514/722 |
| 3,883,665 | 5/1975 | Croix | 514/722 |
| 4,069,346 | 1/1978 | McCarty | 514/722 |
| 4,142,525 | 5/1979 | McCarty | 514/722 |
| 4,154,971 | 5/1979 | Larsen | 514/722 |
| 4,188,405 | 2/1980 | Larsen | 514/722 |
| 4,250,334 | 2/1981 | Coon | 514/722 |
| 4,328,376 | 5/1982 | Berger | 514/722 |
| 4,874,902 | 10/1989 | Huang | 514/722 |
| 4,996,371 | 2/1991 | Halpern | 514/722 |

OTHER PUBLICATIONS

McCarty, American Society of Anesthesiologists, 51:106–110 (1979).
Holaday, American Society of Anesthesiologists, 57:3 (Sep. 1982).
Chemical Abstracts 92:197928n, vol. 92, p. 639 (1980).
Chemical Abstracts, 91:56377m, vol. 91, p. 647 (1979).
Chemical Abstracts, 88:14705n p. 339 (1978).
Chemical Abstracts, 90:105792w vol. 90, p. 107 (1979).
Chemical Abstracts 94:102829k (1981).
Chemical Abstracts 91:140334r (1979).
Holaday et al., Deuteration Reduced Significantly the Biotransformation of Sevoflurane, Am. Soc. of Anesthesiologists, Inc., 57:3 Sep. 1982.

*Primary Examiner*—Jerome D. Goldberg
*Attorney, Agent, or Firm*—Charles F. Lind

[57] ABSTRACT

Use of D2-sevoflurane is disclosed as an inhalational anesthetic. Deuterated sevoflurane possess all of the desirable qualities of sevoflurane as an anesthetic and is metabolized more slowly thereby reducing potentially toxic inorganic fluoride release. More particularly, the compound fluorodideutero methyl 1,1,1,3,3,3-hexafluoropropyl ether is disclosed as well as a method for synthesis.

4 Claims, 2 Drawing Sheets

DEUTERATED SEVOFLURANE AS AN INHALATIONAL ANESTHETIC

This is a divisional of application Ser. No. 08/010,264, filed on Jan. 28, 1993, now abandoned.

BACKGROUND OF THE INVENTION

Halogenated isopropyl derivatives of ether have demonstrated promise for use in the medical field due to their anesthesia inducing properties. Of these, the most successful to date has with fluorinated isopropyl ethers such as sevoflurane (fluoromethyl 1,1,1,3,3,3-hexafluro-2-propyl ether). Sevoflurane has demonstrated rapid induction and recovery from anesthesia when administered by inhalation, making it attractive for use as an anesthetic. Further, sevoflurane is a volatile liquid, non-flammable in air at ambient temperatures and has a lower flammability limit in oxygen of about 11.8 volume-percent, making it safe to use as well. U.S. Pat. No. 3,683,092 to Regan et al. discloses use of sevoflurane as an anesthetic.

While exhibiting many beneficial anesthetic properties, use of sevoflurane as a general inhalational anesthetic has been hampered by its potential nephro-toxicity when metabolized at sufficiently high levels.

Attempts to find other halogenated isopropyl derivatives with beneficial anesthetic properties have led scientists to substitute sevoflurane with other similar moieties. These attempts have not been successful in that several related compounds either do not possess any anesthetic properties, produce only small anesthetic properties, or are toxic. For example, U.S. Pat. No. 3,683,092 discloses that the compound $CH_3OCF(CF_3)_2$ was found to be non-anesthetic up to 8% by volume in oxygen meaning that it would burn at its anesthetic concentration since its lower flammability limit is about 7-8%. Another isomer, trifluoromethyl-2,2,3,3-tetrafluoropropyl ether of Aldrich and Shepard, Jorg., Volume 29, pages 11–15 (1964) has been shown to cause violent convulsions and death in mice at concentrations as low as 0.5%. Yet another isomer, $CHF_2OCH_2CF_2CF_3$ is non-anesthetic up to its lethal concentration and produces convulsions in mice. Still another comparison, it has been found that the isomeric $(CHF_2)_2CF-O-CHF_2$ is a weak anesthetic in which deep anesthesia is not obtained and abnormal electroencephalographic and convulsant activity is observed. Thus it can be seen that there has been little success to dater and a need exists for an anesthetic for use in animals which will possess the advantageous characteristics of sevoflurane while minimizing the concomitant fluoride ion release.

It is an object of the present invention to provide a compound with the beneficial properties of sevoflurane for use as an inhalational anesthetic which will reduce metabolic inorganic fluoride release.

Yet another object of the present invention is to provide a method for inducing anesthesia in patients involving inhalation of deuterated sevoflurane.

It is yet another object of the present invention to provide a method of inducing anesthesia which upon inhalation will produce anesthesia in a patient while being slowly metabolized.

A further object of the present invention is to provide a method of synthesis of fluoro-dideutero-methyl 1,1,1,3,3,3-hexafluoro-2-propyl ether.

Further objects of the invention will be demonstrated from the detailed description of the invention which follows.

SUMMARY OF THE INVENTION

This invention relates to a method of synthesis of deuterated sevoflurane ($D_2$ sevoflurane) and use of the same for anesthetizing animals. $D_2$ sevoflurane is metabolized and subsequently defluorinated at a much slower rate thereby reducing fluoride ion release, while maintaining all of the anesthetic properties of sevoflurane.

A method of inducing anesthesia in animals is disclosed in which D2 sevoflurane is administered by inhalation to the animals. Further, fluoro-dideutero-methyl 1,1,1,3,3,3-hexafluoro-2-propyl ether is synthesized by reacting dimethyl-$D_2$-sulfate with 1,1,1,3,3,3-hexafluoro-isopropanol, which is then reacted with $BrF_3$. Excess $BrF_3$ is then destroyed leaving fluoromethyl 1,1,1,3,3,3-hexafluoro-2-propyl ether.

DETAILED DESCRIPTION OF THE INVENTION

Figure 1:
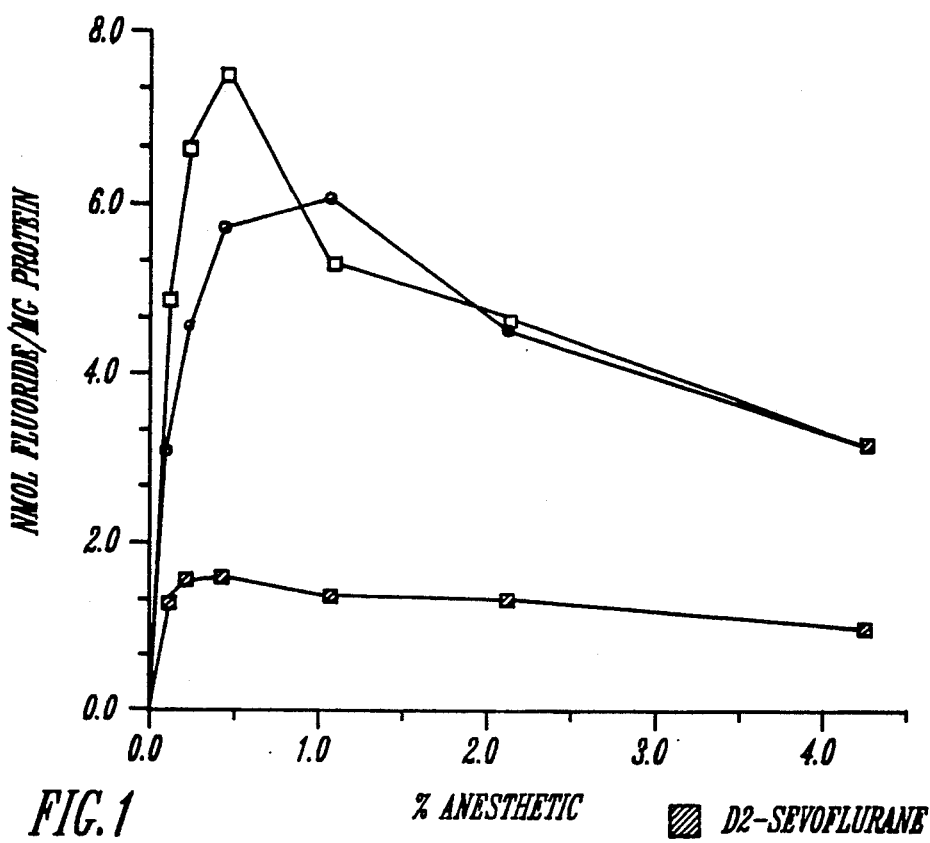
FIG. 1 is a graph depicting concentration dependent defluorination of D2-sevoflurane, sevoflurane, and enflurane in hepatic microsomes from Isoniazid treated rats.

Sevoflurane, or fluoromethyl 1,1,1,3,3,3-hexafluoro-2-propyl ether has the following formula:

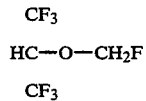

Sevoflurane, upon administration into the body, is metabolized in the liver by cytochrome P450, liberating fluoride and hexafluoroisopropanol. This inorganic fluoride at sufficiently high levels will produce renal dysfunction including polyuria.

In vitro tests have demonstrated that deuterated sevoflurane, particularly with deuterium substitutions at the monofluoro substituted methyl group may be used in animals and as an inhalational anesthetic. One such deuterium substituted derivative found to be especially useful is fluoro-dideuteromethyl-1,1,1,3,3,3-hexafluoro-2-propyl ether of which the following is a formula:

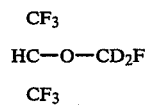

The compound retains all of the beneficial anesthetic qualities of sevoflurane as discussed earlier while at the same time decreasing the exposure to fluoride. This result is surprising due to the fact that isomers of halogenated isopropyl ethers are largely unpredictable with respect to their anesthetic qualities. Further it has been demonstrated that deuterium substitution of ethers used as anesthetic compounds are equally unpredictable in their altered kinetics of metabolism. Another compound which may be useful in the present invention is fluorodideuteromethyl-1,1,1,3,3,3-hexafluoro-2-deutero-2-propyl ether (D3-sevoflurane).

U.S. Pat. No. 4,154,971 to Larsen et al. discloses monodeuterated analogs of 1,1 difluoro 2,2-dihaloethyl difluoromethyl ethers. Accordingly it was discovered that 1,1,2-trifluoro-2-chloro-2-deuteroethyl difluoromethyl ether; 1,1-difluoro-2-deutero-2,2-dichloroethyl difluoromethyl ether; and 1,1,2-1-trifluoro-2-bromo-2-deuteroethyl difluoromethyl ether all exhibited the characteristic of slower metabolism and thus slower defluorination. However, 1,1-difluoro-2,2-dichloro-2-deuteroethyl methyl ether exhibited properties of being more readily metabolized into inorganic fluoride than the undeuterated compound. This unpredictability of deuteration on fluoride ion release has similarly been encountered in other patented systems.

U.S. Pat. No. 4,153,636 similarly discloses deuterated analogs of methoxyflurane wherein 2,2-dichloro-1,1-difluoro-1-methoxy-d3-ethane-d and 2,2-dichloro-1,1-difluoro-1-methoxy-d3-ethane were found to have decreased metabolism and again 1,1 difluoro-2-2-dichloro-2-deuteroethyl methyl ether was found to increase organic flouride release.

The unpredictability of deuteration of anesthetics can also be demonstrated by the deuteration of halothane. Deuteration of halothane inhibits its metabolism to trifluoroacetic acid, but not its metabolism to release fluoride (Sipes IG, Gandolfi AJ, Pohl LR, Krishna G, Brown Jr BR: Comparison of the biotransformation and hepatotoxicity of halothane and deuterated halothane. J. Pharmacol. Exp. Ther. 14:716–720, 1980).

Thus it can be seen that the placement of deuterium atoms in the molecule is critical and highly species specific. $D_2$ sevoflurane with deuterium atoms at the monofluoro methyl group produces an unexpected unpredictable result of decreased rate of metabolism and decreased fluoride ion release while maintaining all the beneficial anesthetic properties of the compound.

According to the present invention, substitution of the hydrogens at the methyl group of sevoflurane with deuterium(D), a heavy isotope of hydrogen, alters the kinetics of metabolism of the compound. The compound retains its anesthetic qualities while being metabolized much more slowly thereby reducing production of inorganic fluoride. Substitution of the hydrogens at the methyl group of sevoflurane eliminates the concentration-dependent peak of fluoride release which occurs upon sevoflurane and enflurane metabolism in microsomes from isoniazid treated rats. Liver mocrosomes from isoniazid treated rats contain the same cytochrome P450 isozyme, P450IIE1, which is present in humans, and is inducible by ethanol and other compounds in humans.

D2-sevoflurane may be synthesized by modification of a method for synthesis of sevoflurane described in U.S. Pat. No. 3,683,092, the disclosure of which is incorporated herein by reference. The method is similar except, Dimethyl-D6-sulfate, instead of dimethyl sulfate is reacted with 1,1,1,3,3,3-hexafluroisopropanol to form trideuteromethyl-1,1,1,3,3,3-hexafluoro-2-propyl ether. The resulting trideuteromethyl-1,1,1,3,3,3-hexafluoro-2-propyl ether is then subsequently monofluorinated by reaction with bromine trifluoride.

D3-sevoflurane is synthesized by reacting D2-sevoflurane with NaOD in $D_2O$. The D2 sevoflurane is deuterated in the 2 propyl position to form fluorodideuteromethyl-1,1,1,3,3,3-hexafluoro-2-deutero-2-propyl ether. All reactions are run with equimolar quantities of reactants preferred, although excesses of one or more of the variants may be used. No critical limits as to temperature or pressure exist, traditionally ambient conditions will be used.

The end product, D2-sevoflurane or D3-sevoflurane may then be administered by the inhalation route to warm blooded, air breathing animals, in an effective anesthetizing amount. Generally the compound is administered in an amount of from about 1 percent to about 5 percent by volume in admixture with from 99 percent to about 95 percent by volume of oxygen or a gaseous mixture containing oxygen and/or other anesthetics in sufficient amount to support respiration.

EXAMPLE 1

To prepare trideuteromethyl-1,1,1,3,3,3-hexafluoro-2-propyl ether, hexafluoroisoproponal (53.3 g) was added to 127 ml of 108 aqueous sodium hydroxide in a Pyrex flask. Dimethyl-D6-sulfate (40 g) was added proportion wise during a thirty-minute period at 5 ° C. while stirring. The reaction mixture was stirred for two hours at room temperature. Distillation of reaction mixture yielded 45 g of trideuteromethyl-1,1,1,3,3,3-hexafluoro-2-propyl ether.

D2-sevoflurane was obtained by placing 8 ml of dried trideuteromethyl-1,1,1,3,3,3-hexafluoro-2-propyl ether in a Pyrex flask. 3 ml of $BrF_3$ were slowly added over a two hour period while stirring. An exothermic reaction occurred, monofluorinating the ether compound. Following the reaction, water was cautiously added to destroy excess $BrF_3$ in the reaction mixture. The reaction mixture was successively washed with dilute sodium sulfate and water. Finally the washed mixture was dried over anhydrous sodium sulfate and yielded 3.1 ml D2-sevoflurane.

EXAMPLE 2

The formation of D2-sevoflurane and determination of its purity were evaluated by two methods of gas chromatography, and by GC-mass spectrometry using the electron impact (EI) and chemical ionization (CI) modes.

The synthesized product exhibited a retention time identical to that of sevoflurane on gas chromatography. D2-sevoflurane chromatography on a carbowax column and using flame ionization detection, showed that the D2-sevoflurane was 99.86% pure. The contaminant at 7.0 minutes and constituting 0.0328 of the sample was identified as hexafluoroisopropanol. Chromatography of the synthesized D2-sevoflurane sample on 10% CO-880 15% LB-550X indicates a purity of 99.9%. This column resolves methyl hexafluoroisopropyl ether or trideuteromethyl hexafluoropropyl ether (retention time of 2.2 minutes) from sevoflurane or D2-sevoflurane (3.3 minutes) and showed that the sample contained no trideuteromethyl-1,1,1,3,3,3-hexafluoro-2-propyl ether (or methyl hexafluoroisopropyl ether).

EXAMPLE 3

Mass spectral analysis of the synthesized D2-sevoflurane was performed on a Nermag R10-10C mass spectrometer in the electron impact and chemical ionization modes. The mass spectrometer was equipped with a DB Wax 30 m×0.2 mm×0.5 μm capillary column for sample introduction.

The electron impact mass spectra of sevoflurane and D2-sevoflurane were observed. The parent ion of either compound was not observed; however, the M-F and M-CF3 fragments occurred. Sevoflurane analysis yielded a M-F fragment with m/z of 181, whereas D2-sevoflurane produced a fragment of m/z 183—two atomic mass units greater. Also, sevoflurane generated a m/z fragment of 131 (M-CF3), whereas D2-sevoflurane showed the corresponding fragment at m/z 133—also two atomic mass units greater. The greater mass of 2 for these fragments confirms that the deuterated compound is fluoro-dideutero-methyl-1,1,1,3,3,3-hexafluoro-2-propyl ether, and the spectra showed that in the D2-sevoflurane sample no sevoflurane was detectable.

Mass spectra of sevoflurane and D2-sevoflurane in the chemical ionization mode showed the parent ion m/z (M+1) of 201 for sevoflurane and 203 for D2-sevoflurane. The parent ion of D2-sevoflurane was 2 atomic mass units greater than that of sevoflurane again confirming D2-sevoflurane.

EXAMPLE 4 — METABOLISM OF D2-SEVOFLURANE

The metabolism of D2-sevoflurane is expected to liberate one fluoride ion for each molecule metabolized by cytochrome P450 since the metabolism of sevoflurane liberates fluoride and hexafluoroisopropanol. To determine the metabolism of D2-sevoflurane relative to sevoflurane and enflurane, these anesthetics were incubated with hepatic microsomes from untreated male Sprague-Dawley rats (200–230 g), or rats treated with isoniazid (80 mg/kg, i.p. for 5 days), or phenobarbital (0.28 in the drinking water for 4 days). Isoniazid induces the cytochrome P450 isozyme P450 2E1 which is thought to metabolize the volatile anesthetics, and phenobarbital induces several forms also shown to play a role in anesthetic metabolism in the rat.

Each incubation vial (6 ml plastic vial) contained 3 ml of 5 mg/ml microsomal protein in a 0.1M sodium phosphate buffer, pH 7.4. An NADPH generating system was added to cytochrome P450 activity, and the NADPH generating system was omitted from control incubations. Anesthetic was added in the quantities indicated and microsomes were incubated for 15 minutes at 37 ° C. Reactions were stopped by placing the vials on ice. Fluoride was assayed in the microsomal mixtures using fluoride ion-specific electrodes (Fisher Scientific) and a 720A Orion pH/ISE meter. Following incubation microsomes were mixed with an equal volume of TISABII buffer for fluoride analysis. Fluoride in each sample was determined from standard curves constructed using fluoride standards ($10^{-7}$ to $10^{-3}$ M NaF) prepared from a commercially available standard solution ($10^{-1}$ M NaF).

Comparison of the defluorination of D2-sevoflurane and sevoflurane in microsomes incubated with an excess of either anesthetic (1 μl anesthetic per incubation) shows that D2-sevoflurane is defluorinated much slower than sevoflurane in all microsomal preparations (table 1).

TABLE 1

COMPARATIVE DEFLUORINATION OF SEVOFLURANE AND $D_2$-SEVOFLURANE BY RAT LIVER MICROSOMES*
nmol $F^-$/mg protein/30 min ± S.E.

| Animal Treatment | Sevoflurane | $D_2$-Sevoflurane |
|---|---|---|
| None | 1.94 ± 0.31 | 0.62 ± 0.60 (68)* |
| Isoniazid | 7.46 ± 0.83 | 1.55 ± 0.39 (79) |
| Phenobarbital | 1.18 ± 0.06 | 0.18 ± 0.03 (84) |

*Numbers in parentheses represent percent decline from sevoflurane values following correction for background (0.43). Values represent the mean and standard errors of triplicate determinations.

Figure 2:
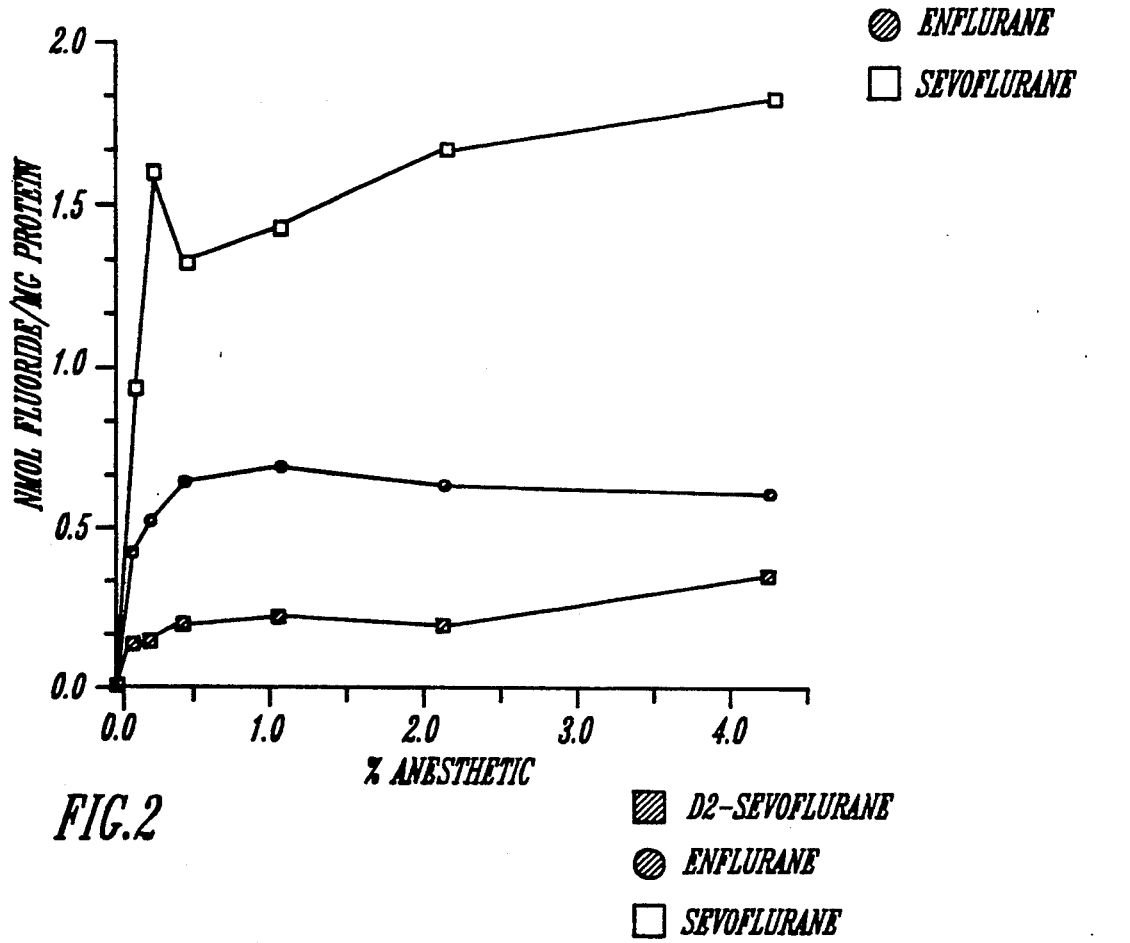
FIG. 2 is a graph depicting concentration dependent defluorination of D2-sevoflurane, sevoflurane, and enflurane in hepatic microsomes from phenobarbital treated rats.

The degrees of inhibited metabolism are 68, 79 and 84% in microsomes from untreated, isoniazid and phenobarbital treated rats, respectively. The concentration-dependent defluorination of D2-sevoflurane, sevoflurane and enflurane, in microsomes from phenobarbital and isoniazid treated rats show that over a wide range of anesthetic concentrations D2-sevoflurane is defluorinated substantially slower than sevoflurane (70–86% less) or enflurane (FIGS. 1 and 2). In microsomes from isoniazid treated rats in which the metabolism of all anesthetics is the greatest due to the induction of P450 IIE1, there was an anesthetic concentration-dependent inhibition of metabolism by sevoflurane and enflurane, but not D2-sevoflurane (FIG. 1). These data suggests a substrate inhibition phenomenon. In microsomes from rats treated with phenobarbital this did not occur (FIG. 2).

EXAMPLE 5 — IN VIVO METABOLISM OF D2-SEVOFLURANE

Untreated rats or rats treated with isoniazid or phenobarbital were exposed to D2-sevoflurane, sevoflurane, or enflurane to determine the relative rates of fluoride production in vivo.

The animals were exposed in a 3.8 L plastic exposure chamber with an atmosphere of 100% oxygen. Male Sprague-Dawley rats (200–220 g, 4 per group) were placed in the chamber and the chamber was flushed with oxygen and sealed. Anesthetic was introduced into the chamber liquid form via an injection port. Quantities were introduced to give initial concentrations of 3% anesthetic (enflurane, 464 μl; sevoflurane and D2-sevoflurane, 524 μl). The rats became anesthetized within 4–6 minutes after introduction of each anesthetic. Oxygen and carbon dioxide were monitored periodically during the exposure period with an Ohmeda 6000 multi-gas monitor.

Following a 30 minute exposure period, the chamber was flushed with 100% oxygen for 5 minutes and the animals quickly awoke. The rats were immediately removed and injected i.p. with 80 mg/kg secobarbital. While anesthetized 3 to 4 ml of blood were withdrawn by cardiac puncture within 15 minutes of termination of anesthetic exposure (within 10 minutes of removal from the chamber). Plasma was prepared and fluoride analyzed as described above.

Figure 3:
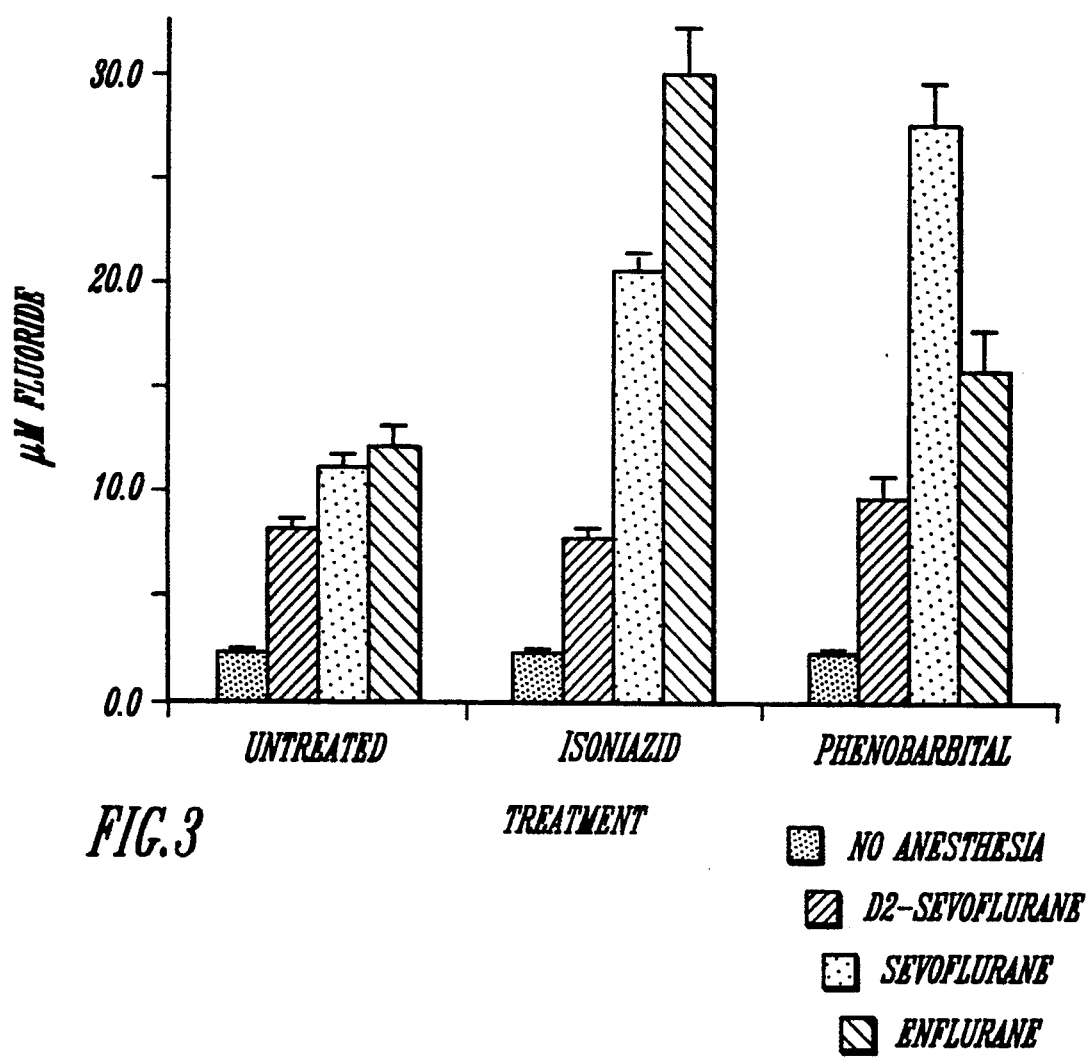
FIG. 3 is a bar graph depicting Plasma fluoride levels in rats anesthetized for 30 minutes with D2-sevoflurane, sevoflurane, and enflurane.

Exposure to D2-sevoflurane resulted in lower plasma fluoride than exposure to either enflurane or sevoflurane (FIG. 3). As compared to The liberation of fluoride from sevoflurane, D2-sevoflurane liberated 61% less in isoniazid treated rats, 66% less in phenobarbital treated animals, and 34 less in untreated rats. D2-sevoflurane also liberated less fluoride than enflurane in vivo. In untreated, and isoniazid and phenobarbital treated rats, the plasma from D2-sevoflurane exposed rats contained 40, 80, and 45%, respectively, less fluoride than enflurane anesthetized animals.

What is claimed is:

1. An inhalation pharmaceutical composition for inducing anesthesia in animals said composition comprising:
   an anesthesia inducing effective amount of fluorodideutero 1,1,1,3,3,3-hexafluoro-2-propyl ether and a pharmaceutically acceptable anesthetic carrier.

2. The composition of claim 1 wherein said carrier is oxygen.

3. The composition of claim 1 where said composition comprises in gaseous mixture from about 1% to 5% of volume of fluorodideutero methyl 1,1,1,3,3,3-hexafluoro-2-propyl ether and 99% to 95% by volume oxygen or oxygen in mixture with other components at a sufficient level to support respiration.

4. The pharmaceutical composition of claim 1 wherein said composition is a gaseous mixture comprising from about 1% to about 5% of volume of said fluorodideutero methyl 1,1,1,3,3,3-hexafluoro-2-propyl ether.

* * * * *